United States Patent [19]
Imbert et al.

[11] Patent Number: 5,880,296
[45] Date of Patent: Mar. 9, 1999

[54] METHOD FOR PREPARING AN OPTICALLY PURE BENZOFURAN CARBOXYLIC ACID AND USE THEREOF FOR PREPARING EFAROXAN

[75] Inventors: Thierry Imbert, Viviers-Les-Montagnes; Patrice Mayer, Castres, both of France

[73] Assignee: Pierre Fabre Medicament, Boulogna, France

[21] Appl. No.: 952,133

[22] PCT Filed: May 9, 1996

[86] PCT No.: PCT/FR96/00697

§ 371 Date: Nov. 10, 1997

§ 102(e) Date: Nov. 10, 1997

[87] PCT Pub. No.: WO96/35682

PCT Pub. Date: Nov. 14, 1996

[30] Foreign Application Priority Data

May 10, 1995 [FR] France .................................. 9505513

[51] Int. Cl.⁶ ...................... C07D 307/85; C07D 405/04
[52] U.S. Cl. ......................................... 549/468; 548/311.4
[58] Field of Search .......................... 549/468; 548/311.4

[56] References Cited

FOREIGN PATENT DOCUMENTS 0 310 745  12/1989  European Pat. Off. .
2 102 422 A  7/1992  United Kingdom .
WO 92/05171  4/1992  WIPO .

OTHER PUBLICATIONS

Lin, J. of Liquid Chromatography, vol. 18, No. 13, pp. 2611–2619, Jul. 1995.

C.R. Edwards et al.: "A Practical Synthesis of 2,3–Dihydro–2–benzofurancarboxylic Acid: A General Route to 2,3–Dihydrobenzofurans"; Journal of Heterocyclic Chemistry, vol. 24, No. 2, Mar./Apr. 1987, pp. 495–496.

Primary Examiner—Bernard Dentz
Attorney, Agent, or Firm—Rockey, Milnamow & Katz, Ltd.

[57] ABSTRACT

A method for preparing an optically pure 2-ethyl-2,3-dihydrobenzofurancarboxylic acid of formula II wherein R is a hydrogen atom, halogen, lower alkyl, lower alkoxy or hydroxy is described.

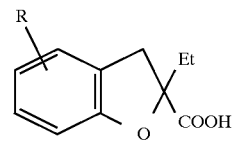

The method comprises separating the racemic mixture by selective crystallization with the suitable optically pure enantiomer of 2-phenylglycinol, in a suitable solvent, whereafter the optically pure, crystallized acid of formula II is isolated and recovered. The invention also provides the optically pure 2-ethyl-2,3-dihydro-benzofurancarboxylic acid derivative thus obtained and the use thereof for the preparation of an optically pure derivative of efaroxan.

9 Claims, No Drawings

METHOD FOR PREPARING AN OPTICALLY PURE BENZOFURAN CARBOXYLIC ACID AND USE THEREOF FOR PREPARING EFAROXAN

This application is a 371 of PCT/FR96/00697 filed May 9, 1996.

The present invention relates to a process for the preparation of an optically pure 2-ethyl-2,3-dihydrobenzofurancarboxylic acid derivative, to the derivative obtained and to its use for the preparation of the corresponding optically pure 2-[2-(2-ethyl-2,3-dihydrobenzofuryl)]-2-imidazoline derivative, in particular efaroxan.

2-[2-(2-Ethyl-2,3-dihydrobenzofuryl)]-2-imidazoline derivatives, in particular efaroxan, are derivatives that antagonize α2-adrenergic receptors and are described in European patent application No. 0,071,368 (Reckitt & Colman) for the treatment of depression or migraine. They are also described for the treatment of Parkinson's disease and neurodegenerative disorders, such as Alzheimer's disease, in WO patent applications No. 95/00145 and No. 95/01791 (Pierre Fabre Medicament).

Their enantiomers are described in WO patent application No. 92/05171, (−)-efaroxan being described in particular for treating diabetes, as a potassium-channel blocker. They are obtained by racemic resolution with dibenzoyl tartaric acid, at the final stage of the synthesis.

The present invention relates to a novel process for the stereospecific synthesis of optically pure 2-[2-(2-ethyl-2,3-dihydrobenzofuryl)]-2-imidazoline derivatives of general formula I

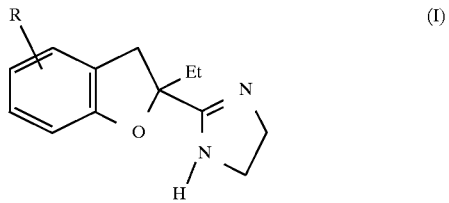

in which R represents a hydrogen or halogen atom or a lower alkyl, lower alkoxy or hydroxyl radical, starting with a corresponding optically pure 2-ethyl-2,3-dihydrobenzofurancarboxylic acid derivative, and to the optically pure derivatives obtained by means of this process.

The synthesis of the derivatives of general formula I is more particularly described in patent application EP-A-0, 071,368 and consists in converting the corresponding 2-ethyl-2,3-dihydrobenzofurancarboxylic acid derivative into an amide of general formula III

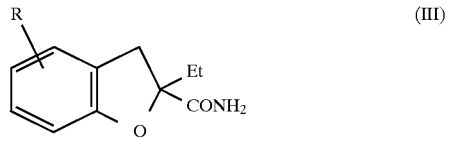

in which R is defined above, and then into the corresponding cyano derivative of general formula IV, by dehydration,

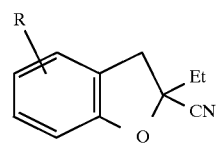

which compound is then converted into the derivative of general formula I, using the usual techniques, with ethylenediamine.

The specific synthetic process according to the invention repeats this general scheme, with the corresponding optically pure 2-ethyl-2,3-dihydrobenzofurancarboxylic acid derivative as starting acid.

The present invention thus relates firstly to the process for the preparation of the starting acid of general formula II

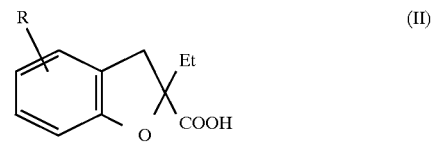

in which R represents a hydrogen or halogen atom or a lower alkyl, lower alkoxy or hydroxyl radical, in which process the racemic mixture is resolved by selective crystallization with the appropriate optically pure enantiomer of 2-phenylglycinol, in a suitable solvent, after which the crystallized optically pure acid of formula II is recovered.

The expression "appropriate optically pure enantiomer of 2-phenylglycinol" is understood to refer to the enantiomer of the acid which allows good separation of the diastereoisomeric salts obtained, one being more stable than the other, and which crystallizing. Thus, the acid of general formula II of R configuration is obtained by selective crystallization with S-(+)-2-phenylglycinol and, conversely, the acid of S configuration is obtained with R-(−)-2-phenylglycinol.

The term "suitable solvent" is understood to refer to any solvent which is capable of assisting the selective crystallization of an enantiomeric salt, while at the same time keeping the other in solution. It will be chosen advantageously from acetone, ethyl acetate, methyl ethyl ketone and mixtures thereof.

The preparation of the racemic acid of general formula II is described in the *Journal of Heterocyclic Chemistry* (1987, 24, 495).

The principle of selective crystallization by formation of diestereoisomeric salts is a known principle. However, it is difficult and hazardous to carry out, in particular when it involves obtaining high optical purity, that is to say greater than or equal to 95%.

One method for separating enantiomers of acids such as the acid of general formula II has been described, and does not involve selective crystallization of diastereoisomeric salts but esterification with optically active menthol (*Chem. Pharm. Bull.*, 1988, 36, 902), which requires an additional step of hydrolysis of the diastereoisomeric ester isolated.

Various chiral amines can be used to form a diastereoisomeric salt with the acid of general formula II, such as, for example, α-methylbenzylamine, or amino alcohols such as optically active phenylalaninol or prolinol.

However, resolution tests on 2-ethyl-2,3-dihydrobenzofurancarboxylic acid with the enantiomers of these three alcohols was unfruitful, only optically pure 2-phenylglycinol allowing a sharp separation of the diastereoisomeric salts by selective crystallization.

S-(+)-2-Phenylglycinol is an amino alcohol which is readily available by reduction of S-(+)-phenylglycine (*Tetrahedron Lett.*, 1992, 33, 5517), and its use for separating certain racemic acids whose structure is remote from the acids of general formula II is described in particular in Japanese patent applications No. 58 029 719, No. 53 018 529 and No. 03 095 138.

The results of these tests of crystallization from ethyl acetate or acetone are reported in Table I below, the purity of the salts crystallized being verified by HPLC (column: chiralx(250×4 mm) β-cyclodextrin; eluent: 1% TEAA buffer, pH 4.1, with 15% MeOH).

TABLE I

| CHIRAL ALCOHOL | RESULT | HPLC |
| --- | --- | --- |
| R-(+)-α-methylbenzyl-amine | crystallization 2 salts | 2 peaks of equal intensity |
| S-(−)-phenylalaninol | crystallization 2 salts | 2 peaks of equal intensity |
| S-(+)-prolinol | no crystallization | — |
| R-(−)-2-phenylglycinol | crystallization with the (−) enantiomer | a single peak |
| S-(+)-2-phenylglycinol | crystallization with the (−) enantiomer | a single peak |

The present invention also relates to the optically pure derivatives of general formula II which can be obtained by the above process, in particular derivatives having an enantiomeric purity greater than or equal to 95%, more particularly greater than 96.5%.

Starting with this optically pure acid, the corresponding derivatives of general formula I are prepared, while conserving the absolute configuration of the product.

The reaction scheme for the preparation of the derivatives of general formula I, starting with the racemic acid, is given overleaf for the preparation of R-(+)-efaroxan, that is to say R represents a hydrogen atom.

The racemic mixture of the acid of formula II in which R=H is placed in acetone, ethyl acetate or methyl ethyl ketone in the presence of a stoichiometric amount of S-(+)-phenylglycinol. After crystallization, the diastereoisomeric salt of (+)-2-ethyl-2,3-dihydrobenzofurancarboxylic acid (A+) and of S-(+)-phenylglycinol (B+) is isolated. The other diastereoisomeric salt formed between (−)-2-ethyl-2,3-dihydrobenzofurancarboxylic acid and S-(+)-phenylglycinol remains in solution. The NMR spectrum of the species (A+) (B+) shows a single compound.

On passage to the free acid form in the presence of hydrochloric acid, the enantiomerically pure (+)-2-ethyl-2, 3-dihydrobenzofurancarboxylic acid is obtained. This acid is converted into the ester by treatment with $SOCl_2$/MeOH and the methyl ester obtained is then treated with aqueous ammonia in order to form the amide which, by dehydration with $P_2O_5$ in toluene, gives the corresponding nitrile. The final stage of the synthesis consists in preparing the imidate from the nitrile, by reaction with a catalytic amount of sodium methoxide, which is then treated with ethylenediamine in a solution of isopropanol and hydrochloric acid, in order to obtain the desired imidazoline.

The overall yield for the preparation of the dextrorotatory isomer of 2-ethyl-2,3-dihydrobenzofuran-2-carboxylic acid is 50% starting from its racemic mixture, and the preparation of (+)-2-[2-(2-ethyl-2,3-dihydrobenzofuryl]-2-imidazoline in hydrochloride form is 50%.

Reaction scheme

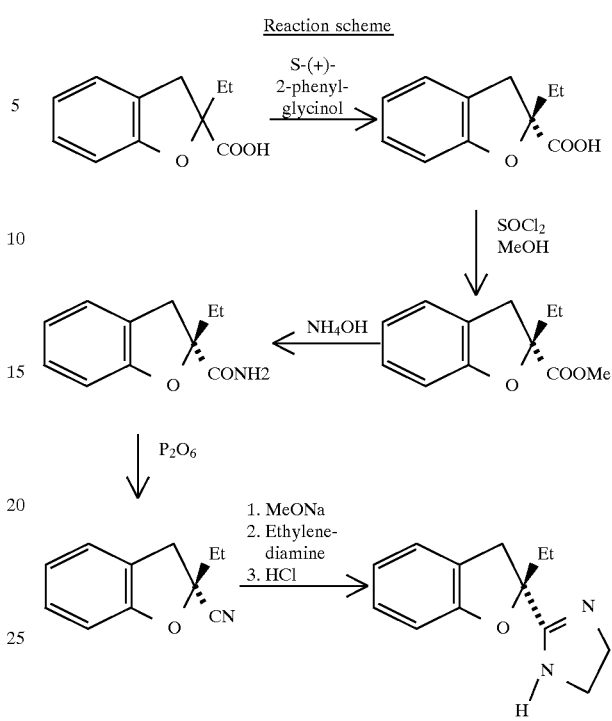

Other characteristics of the process according to the invention will become apparent in the light of the examples below for the selective preparation of R-(+)-efaroxan.

EXAMPLE 1

(+)-2-Ethyl-2,3-dihydro-2-benzofurancarboxylic acid

Racemic 2-ethyl-2,3-dihydro-2-benzofurancarboxylic acid (6 g; 31.2 mmol) is dissolved in 50 ml of ethyl acetate and mixed with a solution of S-(+)-2-phenylglycinol (4.29 g; 31.2 mmol) in 100 ml of ethyl acetate. The crystals are filtered off and recrystallized twice from methyl ethyl ketone in order to give an enantiomeric purity of 96.6%; $[\alpha]D=+55.9°$ (C=0.3; MeOH). The free acid is obtained by extraction in $CH_2Cl_2$ and 1N HCl in order to give 1.52 g (50%) of crystals which are used in step 2 of Example 2.

Starting with the same racemic acid but using R-(−)-2-phenylglycinol, the diastereoisomeric salt is obtained after two recrystallizations from acetone and methyl ethyl ketone. Crystals are obtained whose optical rotation is: $[\alpha]D=-55.70°$ (C=0.26; MeOH).

EXAMPLE 2

Methyl (+)-2-ethyl-2,3-dihydro-2-benzofurancarboxylate

The enantiomerically pure acid obtained in Example 1 is treated with 0.5 ml of $SOCl_2$ in 100 ml of methanol, at room temperature overnight, followed by evaporation, to give 1.5 g of methyl ester.

EXAMPLE 3

(+)-2-Ethyl-2,3-dihydro-2-benzofurancarboxamide

The ester from the above stage is placed in 50 ml of concentrated aqueous ammonia solution, with stirring at room temperature. After evaporation, 1.38 g of crude amide compound are obtained, which product is used in the following step.

EXAMPLE 4

(+)-2-Ethyl-2,3-dihydro-2-cyanobenzofuran

The amide of Example 3 is treated with 5 g of $P_2O_5$ in 50 ml of refluxing toluene for 16 h. After separation of the phases by settling and the usual extraction, 1.06 g of nitrile are obtained, which product is used directly in the following step.

EXAMPLE 5

(+)-2-[2-(2-Ethyl-2,3-dihydrobenzofuryl)]-2-imidazoline hydrochloride

The nitrile obtained in Example 4 (1 g) is placed in ethanol (50 ml) and treated with a catalytic amount of sodium methoxide at 0° C., and then left at room temperature for six days. At the end of the reaction (TLC), 0.582 ml of ethylenediamine is added to the reaction medium, followed by a 5 N solution of isopropanol saturated with hydrogen chloride gas. The reaction mixture is stirred for four days and is then extracted with $CH_2Cl_2$ and 1 N sodium hydroxide solution, and 702 mg of the compound in base form are thus obtained, the hydrochloride of which is formed in ether by addition of 0.62 ml of isopropanol HCl (5 N). Recrystallization from acetonitrile gives the hydrochloride in the form of pure crystals.

m.p.=246° C.; [α]D [sic]=+99.32 (C=0.29; MeOH) IR (KBr): ν $cm^{-1}$=2977, 2901, 1603, 1480, 1460 $^1$H-NMR (DMSO): δ=0.90 (t, 3H, J=7.2 Hz, $CH_3$); 1.95–2.2 (m, 2H, $CH_2$ethyl); 3.35 (d, 1H, J=16.7 Hz, $ArCH_A$); 3.57 (d=1H, J=16.7 Hz, $ArCH_B$); 3.85 (s, 4H, $2CH_2$imidazoline); 6.86–6.95 (m, 2H, $H_5$–$H_7$); 7.13–7.25 (m, 2H, $H_4$–$H_6$) ; 9.20 (d, 1H, NH).

Enantiomeric purity: 99.9%

Tests of separation of the racemic acids II having a substituent R=4–F and R=5–F lead to the production of the corresponding, optically pure, dextrorotatory acids II. These acids are used to prepare the corresponding, enantiomerically pure compounds derived from general formula I, which also form part of the present invention:

(+)-2-[2-(2-ethyl-4-fluoro-2,3-dihydrobenzofuryl)]-2-imidazoline hydrochloride;

(+)-2-[2-(2-ethyl-5-fluoro-2,3-dihydrobenzofuryl)]-2-imidazoline hydrochloride.

We claim:

1. Process for the preparation of an optically pure 2-ethyl-2,3-dihydrobenzofurancarboxylic acid derivative of formula II

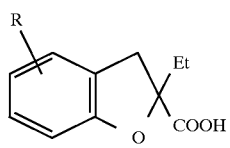
(II)

in which R represents a hydrogen or halogen atom or a lower alkyl, lower alkoxy or hydroxyl radical, in which process the racemic mixture is resolved by selective crystallization with the appropriate optically pure enantiomer of 2-phenylglycinol, in a suitable solvent, after which the crystallized optically pure acid of formula II is recovered.

2. Process according to claim 1, wherein the acid of formula II of R-(+) configuration is obtained by selective crystallization with S-(+)-2-phenylglycinol.

3. Process according to claim 1 wherein the solvent is selected from acetone, ethyl acetate, methyl ethyl ketone and mixtures thereof.

4. Optically pure 2-ethyl-2,3-dihydrobenzofurancarboxylic acid of formula II which can be obtained by the process according to claim 1.

5. Optically pure 2-ethyl-2,3-dihydrobenzofurancarboxylic acid of formula II,

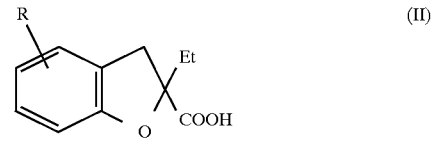
(II)

6. Optically pure R-(+)-2-ethyl-2,3-dihydrobenzofurancarboxylic acid according to either of claim 5.

7. Process for the preparation of an optically pure 2-[2-(2-ethyl-2,3-dihydrobenzofuryl)]-2-imidazoline derivative of formula I

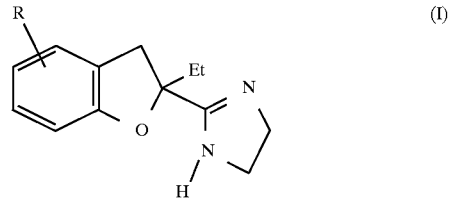
(I)

in which R represents a hydrogen or halogen atom or a lower alkyl, lower alkoxy or hydroxyl radical, by conversion of the optically pure 2-ethyl-2,3-dihydrobenzofurancarboxylic acid derivative of corresponding formula II, defined according to one of claim 4.

8. Process according to claim 7, characterized in that the 2-[2-(2-ethyl-2,3-dihydrobenzofuryl)]-2-imidazoline derivative of formula I and the corresponding optically pure 2-ethyl-2,3-dihydrobenzofurancarboxylic acid of formula II are each of R configuration.

9. Process according to claim 8, characterized in that R represents a hydrogen atom and the 2-[2-(2-ethyl-2,3-dihydrobenzofuryl)]-2-imidazoline derivative of formula I and the corresponding optically pure 2-ethyl-2,3-dihydrobenzofurancarboxylic acid of formula II are each of R configuration and dextrorotatory (+).

* * * * *